(12) United States Patent
Schindler

(10) Patent No.: US 8,904,703 B2
(45) Date of Patent: Dec. 9, 2014

(54) HERBICIDE METHOD AND APPARATUS

(76) Inventor: Jacob Harrison Schindler, Lake Park, GA (US)

( * ) Notice: Subject to any disclaimer, the term of this patent is extended or adjusted under 35 U.S.C. 154(b) by 548 days.

(21) Appl. No.: 13/065,861

(22) Filed: Mar. 31, 2011

(65) Prior Publication Data

US 2012/0252671 A1 Oct. 4, 2012

(51) Int. Cl.
*A01N 59/00* (2006.01)
*A01M 21/04* (2006.01)

(52) U.S. Cl.
CPC ............ *A01M 21/043* (2013.01); *A01N 59/00* (2013.01); *Y10S 47/10* (2013.01)
USPC ........... 47/57.5; 47/DIG. 10; 175/21; 175/71; 175/212; 175/215; 175/218; 175/315; 175/324; 175/325.5; 175/424

(58) Field of Classification Search
CPC ........... A01G 29/00; A01G 7/06; A01G 7/00; A01G 11/00; A01M 21/043; A01M 21/04; A01M 21/00; A01M 7/006; A01M 7/005; A01M 7/0021; A01M 7/0017; A01M 7/0003; A01M 7/0046; A01M 7/0039; A01M 7/0035; A01M 7/0032; A01M 7/0025; E21B 7/206; E21B 7/205; E21B 7/20; E21B 7/00; E21B 10/61; E21B 10/60; E21B 10/00; E21B 17/16; E21B 17/00; E21B 19/24; E21B 19/00; E21B 21/16; E21B 21/14; E21B 21/10; E21B 21/00; E21B 41/0078; E21B 41/00; E21B 2010/607; E21B 2010/60; E21B 2010/00; E21B 2021/005; E21B 2021/00; E21B 2034/00; E21B 2034/007

USPC .......... 47/57.5, 1.5, DIG. 10; 175/424, 19, 21, 175/65, 71, 212, 207, 215, 218, 315, 324, 175/325.1, 325.5, 320
See application file for complete search history.

(56) References Cited

U.S. PATENT DOCUMENTS

| | | | |
|---|---|---|---|
| 1,677,153 A | 7/1928 | Spencer | |
| 1,814,445 A | 7/1931 | Irish | |
| 1,814,446 A | 7/1931 | Irish | |
| 1,991,930 A | 2/1935 | Hope | |
| 3,071,200 A | 1/1963 | Kuhl | |
| 3,106,148 A | 10/1963 | Bothe et al. | |
| 3,142,273 A | 7/1964 | Dilts | |
| 3,640,234 A | 2/1972 | Carroll et al. | |
| 3,685,536 A * | 8/1972 | Bake et al. .................... | 137/338 |

(Continued)

OTHER PUBLICATIONS

Michael Curtis "Jacob Schindler Revolutionizing Kudzu Eradication" Newspaper "The Madison Enterprise Record" Nov. 28, 2008, pp. 1 and 3A. Madison, FL, USA.

(Continued)

*Primary Examiner* — Christopher J Novosad
(74) *Attorney, Agent, or Firm* — Brian D. Bellamy

(57) ABSTRACT

Apparatus and method for boring into the earth near a Kudzu vine root system to apply herbicidal helium gas to the roots and eradicate the Kudzu vine. The technique uses a perforated tube with a drill bit that protrudes from one end of the tube to bore into the earth near the vine roots. Boring is stopped when all of the tube perforations are below the earth's surface. About 0.5 cubic meters of helium gas are applied to flow through the tube enabling the helium gas to flow out through the tube perforations and attack the Kudzu vine through the vine's root system.

3 Claims, 1 Drawing Sheet

(56) References Cited

U.S. PATENT DOCUMENTS

| | | | |
|---|---|---|---|
| 3,832,803 A | * | 9/1974 | Blake et al. ............... 47/57.5 |
| 4,429,647 A | | 2/1984 | Zinck |
| 4,697,952 A | | 10/1987 | Maddock |
| 5,735,076 A | | 4/1998 | Masui et al. |
| 5,802,996 A | | 9/1998 | Baxter |
| 6,185,865 B1 | | 2/2001 | Soli et al. |

OTHER PUBLICATIONS

"Schindler Offers Hope to Kudzu Delimma [sic]," "The Linerboard Leader" (Magazine), Spring, 2008, pp. 14 to 16, Packaging Corp. of America, Valdosta, GA, USA.

Bill Warhop "The Kudzu Kid," "Atlanta Magazine," Jan. 2011, pp. 72 to 75, 134 and 135.

Jacob Schindler "The Effects of Various Gases on Kudzu Growth," Paper, undated, pp. 1-13, Lowndes Middle School, Valdosta, GA, USA.

Jacob Schindler, "The Production of Helium Injection Prototype for the Eradication of Kudzu/Pueraria Species" Symposium, Oct. 21, 2010, pp. 1 to 19, National FFA Conven.

David J. Moorhead et al. "Controlling Kudzu in CRP Stands" Paper, Mar. 31, 2005, pp. 1-6, The University of Georgia, Warnell School of Forest Resources, Georgia, USA.

Arthur E. Miller "Biological Methods for Kudzu Control", Paper, USDA Animal and Plant Health Center, Sep. 2005, p. 1-3.

Masuda, M. et al. "Carbon and Helium Ion Beam Irradiation Effects on Seedling and Plant Characters of Tomato" Science Links Japan, 2006-2007, Japan Science & Tech. Ag., p. 1.

Jacob Schindler The Effect of Helium on Kudzu (*Pueraria* Species) a 3rd Year in Vivo Experiment, Paper, Apr. 23, 2010, pp. 1-13, Georgia FFA Association, Macon, Georgia.

\* cited by examiner

HERBICIDE METHOD AND APPARATUS

BACKGROUND OF THE INVENTION

This invention relates to method and apparatus for destroying Kudzu vines (*pueraria lobata*) and, more particularly, to the application of helium gas to Kudzu vine root systems through a perforated tube driven into the soil close to the vine's roots, and the like.

DESCRIPTION OF THE PRIOR ART

Clearly, there is a need to eradicate, or at least to control the rampant growth of the Kudzu vine in southeastern United States. Illustratively, this plant grows very swiftly—as much as sixty feet in one year, thereby not only choking and depriving the surrounding trees and plant life of moisture and nutrients, but also promoting forest fires.

Because this vine grows in proximity to other more desirable plant life an herbicide to be effective in controlling or eradicating the Kudzu vine must be specific to the Kudzu plant and must not destroy surrounding plant growth. The direct application of helium, as a gas, to Kudzu root systems was found to have the potential to destroy this weed selectively in the presence of profuse plant growth without adversely affecting other nearby plants.

There are at least two theories extant that attempt to explain the herbicidal effect that helium gas has on the Kudzu vine. For example, one theory hypothesizes that chemically inert helium, concentrating in the plant, forms an embolism that obstructs the flow of water and nutrients within the vine. Another theory proposes that chemically inert helium acts as a possible carrier molecule, also with an herbicidal effect on the Kudzu vine.

In these circumstances with a great deal of effort it has been ascertained that helium is the herbicidal agent of choice for the Kudzu vine. And, on establishing helium as a specific Kudzu herbicide it is then necessary to develop a suitable apparatus for applying helium to the vine in a lethal concentration.

In the past, a ditch had been excavated and a perforated vinyl pipe horizontally disposed in the ditch to discharge the helium near a Kudzu vine root system. The pipe then was coupled to large helium tanks on the earth's surface. This technique is expensive and cumbersome in that it requires excavation equipment and frequently involves the burden of carrying heavy tanks of helium into densely overgrown woods.

To provide a truly acceptable device for applying the helium gas herbicide to a Kudzu vine, a number of important criteria must be satisfied. For instance the device must be lightweight, sturdy and easy to use. Further in this connection, the structure must be proof not only against corrosion, but also strong enough to drill through soil while coping with rocks and stones without bending or otherwise deforming. The length of the device, moreover, must be adequate to reach deep Kudzu roots.

Thus, there continues to be a need to provide an efficient system for applying helium gas to the Kudzu root structure that is portable, inexpensive and effective in eliminating the Kudzu weed.

BRIEF SUMMARY OF THE INVENTION

The foregoing need for a suitable herbicidal helium gas delivery system is satisfied to a large extent through the practice of the invention. For example, a tube has a drill bit protruding from one end of the tube. A shank that ordinarily is engaged by a drill's chuck, protrudes from the opposite end of the tube.

A nipple, to establish gas communication between an externally mounted valve and the interior of the tube is attached to the tube and close to the shank end of the tube. Two sets of perforations are formed, each along the length of the tube and on opposite sides of the tube to enable gas within the tube to penetrate the surrounding soil. Each of these sets of perforations, moreover, are spaced below the nipple and valve combination.

A power drill is coupled to the shank and is activated to enable the drill bit to bore into the soil near a selected Kudzu vine root. The drill is deactivated on reaching a suitable depth in which at least all of the perforations formed along the length of the tube are well below the earth's surface. A small canister of helium is coupled through a flexible conduit to the inlet side of the valve and the valve is opened to enable the helium to flow into the tube, through the sets of perforations, and out into the surrounding soil in order to reach the Kudzu vine's root system. On exhausting the helium content of two canisters, producing in total about one half cubic meter of helium at standard pressure and temperature, the last canister is disconnected from the valve, and the direction of drill rotation is reversed to draw the tube out of the soil in which it is lodged and the tube, on complete withdrawal, is now ready for use elsewhere.

For a more detailed appreciation of the invention, reference is made to the following description of a preferred embodiment of the invention when taken with the drawing. The scope of the invention, however, is limited only through the claims appended hereto.

DETAILED DESCRIPTION OF THE INVENTION

Figure 1:
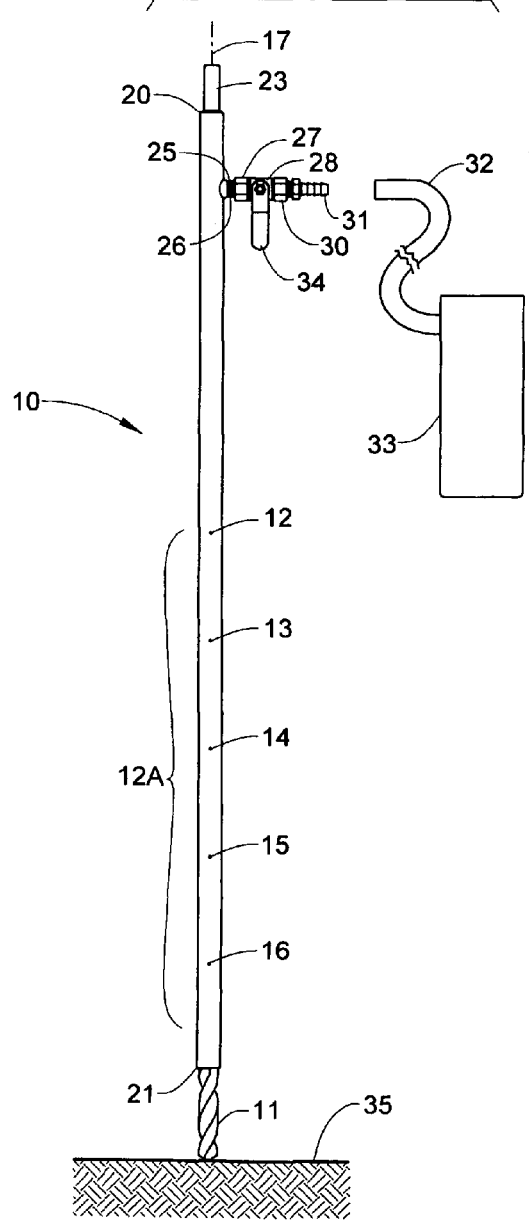
FIG. 1 of the drawing is a front elevation of an illustrative embodiment of the invention.

As illustrated in the drawing, a hollow tube 10 of stainless steel, copper, carbon fiber reinforced plastic or other suitable material, preferably of about 1.8 cm in outside diameter and about 1.6 cm inside diameter is approximately 87 cm in length. A first set 12A of five gas release perforations 12, 13, 14, 15 and 16, each of about 0.16 cm in diameter are formed in the tube 10 in alignment with longitudinal tube axis 17. The perforation 12 is spaced about 38 cm from tube end 20 and each of the subsequent perforations 13, 14, 15 and 16 are spaced, commencing with the perforation 13 and progressing toward opposite tube end 21 by successive distances of about 7.6 cm, measured each from the next adjoining of the perforations.

Figure 2:
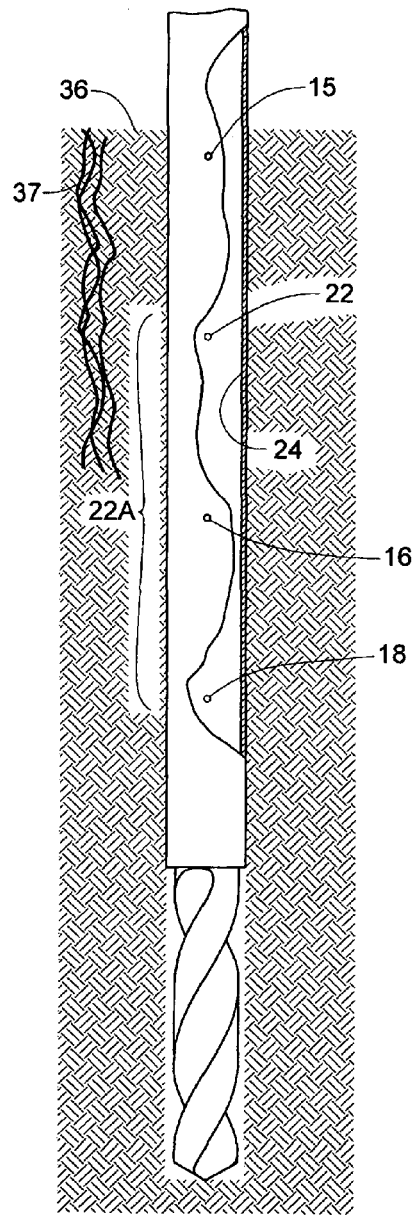
FIG. 2 is an enlarged view of the lower portion of the embodiment of the invention shown in FIG. 1.

A set 22A (FIG. 2) of five gas release perforations (of which only perforations 18 and 22 are shown in the drawing) are similar to the first set 12A of the perforations 12 through 16. The set 22A, however, is formed on the side of the tube 10, that is opposite to the side of the tube 10 occupied by the perforation set 12A. The perforations in the second set 22A, also are in alignment with the longitudinal tube axis 17 but are staggered relative to the spacing for the first set 12A of the perforations 12 through 16. Thus, the gas release perforation 22 in the second set 22A is spaced 3.8 cm from the perforation 15 and 3.8 cm from the next adjacent perforation 16 in the first perforation set 12A.

The tube end 20 (FIG. 1) has a shank 23 that is welded or otherwise appropriately secured in hollow center 24 (FIG. 2) of the tube 10. As shown, the shank 23 is designed for engagement by a chuck (not shown) for a battery powered drill (also not shown). A sears "Craftsman" hand impact drill, identified through product number 11581, has been satisfactory for use in accordance with the invention.

To establish fluid communication with the hollow center 24 (FIG. 2) of the tube 10, a nipple 25 (FIG. 1) is brazed, or otherwise joined to a matching opening (not shown in the drawing) in the surface of the tube 10. For the purpose of the invention, a galvanized steel screw nipple is preferred for this use. A threaded end 26 protrudes from the nipple 25 to engage a corresponding female thread in valve outlet 27 to establish a gas-tight connection with a valve 28.

It has been found that a 0.6 cm inside diameter brass ball valve, manufactured by Mueller/B&K and identified through product number 107-701 has been suitable for helium gas flow control in accordance with the invention as described subsequently. Inlet 30 for the valve 28, moreover, has a gas adapter 31 with a surface that is serrated in order to make a gas tight connection between the valve 28 and one end of a flexible clear vinyl conduit 32. In turn, the other end of the conduit 32 establishes gas communication with a small, portable helium canister 33.

With respect to the helium canister 33, two canisters, each having 0.25 cubic meters of helium gas under a pressure (when full) of at least 260 pounds per square inch (PSI), for a total of 0.5 cubic meters at standard atmospheric pressure and temperature provide a suitable herbicidal effect when the canister 33 (only one of which canisters is shown in the drawing) are applied in sequence in accordance with the invention. Further in this connection, helium canisters sold by Balloon Time under product number SKU 114710 with a helium purity of 94% to 96% were used with the method and apparatus described herein and have produced the desired Kudzu vine herbicidal result. Naturally, for Kudzu eradication over larger areas, large helium tanks also have been used with great success.

In operation, the chuck on a battery powered drill (not shown in the drawing) connects the drill to the drill shank 23. The tube 10 is placed near a Kudzu vine stem as that stem protrudes above the earth with the longitudinal tube axis 17 of the tube 10 generally perpendicular to the surface of earth 35 to press drill bit 11 against the soil. Preferably a 1.6 cm diameter black oxide coated drill bit is suitable for this purpose.

The drill is energized and the torque applied by the drill turns the tube 10 and the drill bit 11, causing the drill bit 11 and the balance of the tube 10 to bore into the earth. The drilling is continued until all of the perforations in the two perforation sets 12A and 22A are well below the surface of the earth, whereupon the drill is deactivated and disconnected from the shank 23.

A first of the two helium canisters 33 is then coupled through the flexible conduit 32 and the gas adapter 31 to the valve 28. Valve handle 34 is shifted to a valve open position and helium gas flows from the canister 33, through the valve 28 and into the hollow center 24 (FIG. 2) of the tube 10.

Once in the tube 10, under the gas pressure supplied by the helium canister 33, the helium gas disperses into soil 36 surrounding the tube 10 through the perforations in the sets 12A and 22A and migrates in the soil 36 to Kudzu vine root 37. Upon depletion of the helium in the canister 33, the valve handle 34 is shifted to close the valve 28. With the valve 28 closed, the helium canister 33 is removed and replaced with a fresh, full helium canister, whereupon the process practiced with the first canister 33 is repeated until the helium in the second canister also is depleted.

Field trials have shown that four weeks after exposure to helium in the manner described above, in two test sites all of the Kudzu vines so treated were destroyed. At a third test site an estimated 95% of the Kudzu was destroyed. The effect, moreover, of this Kudzu vine treatment on surrounding plant life was found to be surprisingly beneficial, as observed not only through the growth of new grass but also through new leaf growth.

After treatment, the second, depleted canister and the associated flexible conduit 32 are detached from the gas adapter 31. The drill is reconnected to the shank 23 and the drill is reenergized, albeit with the torque reversed, to enable the tube and the bit to be withdrawn from the ground. When treatment is complete and the tube 10 and the associated drill bit 11 have been withdrawn from the earth, the spoil (not shown in the drawing) from the original drilling is used to fill the hole left by the tube and the drill bit.

In passing it can be inferred from the accumulated data that other inert gases—argon, neon, krypton and xenon, for instance, might also be commercially acceptable Kudzu vine herbicides.

What is claimed is:

1. An apparatus for applying a herbicidal inert gas to the roots of a Kudzu vine comprising a perforated tube having two opposite ends and a hollow interior, said perforated tube having a plurality of perforations including first and second sets of perforations, said perforations penetrating from outside said tube to the hollow interior, said perforations being aligned with said tube length, and said first and second sets being formed respectively on opposite sides of said tube, a drill bit secured in one end of said tube, a drill shank secured in said opposite tube end from the end said drill bit is secured, a nipple on said tube to establish inert gas communication with said hollow interior, a valve coupled to said nipple for controlling the inert gas flow into said hollow interior, said plurality of perforations spaced below the nipple and the valve on the perforated tube, whereby the inert gas within said hollow interior disperses through said tube perforations to the Kudzu vine roots.

2. An apparatus according to claim 1 further comprising an inert gas canister for selective coupling to said valve.

3. An apparatus according to claim 2 further comprising a flexible conduit for establishing inert gas communication between said inert gas canister and said valve.

* * * * *